US007900632B2

(12) United States Patent
Cook

(10) Patent No.: US 7,900,632 B2
(45) Date of Patent: Mar. 8, 2011

(54) LARYNGEAL MASK WITH ESOPHAGEAL BLOCKER AND BITE BLOCK

(75) Inventor: Daniel J. Cook, St. Louis, MO (US)

(73) Assignee: Cookgas, L.L.C., St. Louis, MO (US)

( * ) Notice: Subject to any disclaimer, the term of this patent is extended or adjusted under 35 U.S.C. 154(b) by 146 days.

(21) Appl. No.: 11/465,713

(22) Filed: Aug. 18, 2006

(65) Prior Publication Data
US 2008/0041392 A1 Feb. 21, 2008

(51) Int. Cl.
*A61M 16/04* (2006.01)
(52) U.S. Cl. .................................... 128/207.14
(58) Field of Classification Search ............ 128/200.24, 128/107.14, 207.15; 604/96.01, 101.01; 606/196
See application file for complete search history.

(56) References Cited

U.S. PATENT DOCUMENTS

| 678,814 | A | 7/1901 | Riggs |
| 1,345,425 | A | 7/1920 | Wells |
| 2,335,741 | A | 11/1943 | Contaldi |
| 2,787,010 | A | 4/1957 | Uphoff |
| 3,139,088 | A | 6/1964 | Galleher, Jr. |
| 3,434,100 | A | 3/1969 | Dykzeul |
| 3,606,669 | A | 9/1971 | Kemble |
| 3,734,100 | A | 5/1973 | Walker et al. |
| 3,756,601 | A | 9/1973 | Frey et al. |
| 3,945,069 | A | 3/1976 | Cecil |
| 4,146,034 | A | 3/1979 | Gupta |
| 4,231,365 | A * | 11/1980 | Scarberry ............... 128/207.15 |
| 4,327,720 | A * | 5/1982 | Bronson et al. ........ 128/207.15 |
| 4,340,046 | A | 7/1982 | Cox |
| 4,388,076 | A | 6/1983 | Waters |
| 4,444,201 | A | 4/1984 | Itoh |
| 4,509,512 | A | 4/1985 | LeClercq |
| 4,509,514 | A | 4/1985 | Brain |
| 4,520,810 | A | 6/1985 | Weiss |
| RE31,948 | E | 7/1985 | Deutsch et al. |
| 4,540,959 | A | 9/1985 | Saad |
| 4,582,056 | A | 4/1986 | McCorkle, Jr. |
| 4,593,687 | A | 6/1986 | Gray |
| 4,661,028 | A | 4/1987 | Sanger |
| 4,674,496 | A | 6/1987 | Svadijan et al. |
| 4,751,922 | A | 6/1988 | DiPietropolo |
| 4,791,923 | A | 12/1988 | Shapiro |
| 4,825,861 | A | 5/1989 | Koss |
| 4,863,439 | A | 9/1989 | Sanderson |
| 4,872,438 | A | 10/1989 | Shah |
| 4,895,533 | A | 1/1990 | Yagi |
| 4,919,127 | A | 4/1990 | Pell |
| 4,995,388 | A * | 2/1991 | Brain ..................... 128/207.15 |

(Continued)

OTHER PUBLICATIONS

Tooth Numbering Systems, www.ada.org/public.topics/tooth_number.asp, printed Aug. 11, 2006.

(Continued)

Primary Examiner — Danton DeMille
(74) Attorney, Agent, or Firm — Lewis, Rice & Fingersh, L.C.

(57) ABSTRACT

A supraglottic airway of the type used to facilitate lung ventilation and the insertion of endo-tracheal tubes or related medical instruments through a patient's laryngeal opening including a guide structure for use in deploying an esophageal blocker into the patient's esophagus and additionally or alternatively including a bite block for inhibiting a patient from biting an internal passageway in the respiratory tube of the airway closed.

29 Claims, 9 Drawing Sheets

U.S. PATENT DOCUMENTS

| | | | |
|---|---|---|---|
| 5,024,220 A | 6/1991 | Holmgreen et al. | |
| 5,033,919 A | 7/1991 | Choe | |
| 5,037,251 A | 8/1991 | Roth | |
| 5,042,475 A | 8/1991 | LaBombard | |
| 5,071,413 A | 12/1991 | Utterberg | |
| 5,197,463 A | 3/1993 | Jeshuran | |
| 5,218,970 A | 6/1993 | Turnbull et al. | |
| 5,222,487 A | 6/1993 | Carr et al. | |
| 5,241,956 A | 9/1993 | Brain | |
| 5,253,658 A | 10/1993 | King | |
| 5,277,178 A | 1/1994 | Dingley | |
| 5,279,610 A | 1/1994 | Park et al. | |
| 5,282,464 A | 2/1994 | Brain | |
| 5,303,697 A | 4/1994 | Brain | |
| 5,324,080 A | 6/1994 | McNaughton et al. | |
| 5,326,196 A | 7/1994 | Noll | |
| 5,340,165 A | 8/1994 | Sheppard | |
| 5,355,879 A | 10/1994 | Brain | |
| 5,391,248 A | 2/1995 | Brain | |
| 5,392,774 A | 2/1995 | Sato | |
| 5,393,101 A | 2/1995 | Matkovich | |
| 5,477,851 A | 12/1995 | Callaghan et al. | |
| 5,477,852 A | 12/1995 | Landis et al. | |
| 5,509,408 A | 4/1996 | Kurtis | |
| 5,513,627 A * | 5/1996 | Flam | 128/200.26 |
| 5,520,175 A | 5/1996 | Fry | |
| 5,527,316 A | 6/1996 | Stone | |
| 5,529,582 A | 6/1996 | Fukuhara | |
| 5,545,048 A | 8/1996 | Maeda | |
| 5,546,937 A | 8/1996 | Stuart et al. | |
| 5,562,371 A | 10/1996 | Reed | |
| 5,562,673 A | 10/1996 | Koblish et al. | |
| 5,569,222 A | 10/1996 | Haselhorst et al. | |
| 5,579,762 A | 12/1996 | Lee | |
| 5,584,290 A | 12/1996 | Brain | |
| 5,588,424 A * | 12/1996 | Insler et al. | 128/207.15 |
| 5,590,643 A | 1/1997 | Flam | |
| 5,623,921 A | 4/1997 | Kinsinger et al. | |
| 5,632,271 A | 5/1997 | Brain | |
| RE35,531 E | 6/1997 | Callaghan et al. | |
| 5,643,174 A | 7/1997 | Yamamoto et al. | |
| 5,653,231 A | 8/1997 | Bell | |
| 5,655,519 A | 8/1997 | Alfery | |
| 5,682,880 A | 11/1997 | Brain | |
| 5,711,296 A | 1/1998 | Kolobow | |
| 5,713,348 A | 2/1998 | Pell | |
| 5,720,749 A | 2/1998 | Rupp | |
| 5,743,258 A | 4/1998 | Sato | |
| 5,771,889 A | 6/1998 | Pagan | |
| 5,772,643 A | 6/1998 | Howell et al. | |
| 5,787,879 A | 8/1998 | Gibson | |
| 5,791,341 A | 8/1998 | Bullard | |
| 5,871,012 A | 2/1999 | Neame et al. | |
| 5,878,745 A | 3/1999 | Brain | |
| 5,881,726 A | 3/1999 | Neame | |
| 5,896,858 A | 4/1999 | Brain | |
| 5,937,859 A | 8/1999 | Augustine et al. | |
| 5,937,860 A | 8/1999 | Cook | |
| 5,947,120 A | 9/1999 | Bailey | |
| 5,961,489 A | 10/1999 | Hirota | |
| 5,979,445 A | 11/1999 | Neame et al. | |
| 5,983,897 A | 11/1999 | Pagan | |
| 5,988,167 A | 11/1999 | Kamen | |
| 6,003,514 A | 12/1999 | Pagan | |
| 6,012,452 A | 1/2000 | Pagan | |
| 6,021,779 A | 2/2000 | Pagan | |
| 6,050,264 A | 4/2000 | Greenfield | |
| 6,086,603 A | 7/2000 | Termin et al. | |
| 6,095,144 A | 8/2000 | Pagan | |
| 6,110,143 A | 8/2000 | Kamen | |
| 6,116,243 A | 9/2000 | Pagan | |
| 6,119,695 A | 9/2000 | Augustine et al. | |
| 6,196,224 B1 | 3/2001 | Alfery | |
| 6,240,922 B1 | 6/2001 | Pagan | |
| 6,261,401 B1 | 7/2001 | Pagan | |
| 6,311,688 B1 | 11/2001 | Augustine et al. | |
| 6,318,367 B1 * | 11/2001 | Mongeon | 128/207.15 |
| 6,338,343 B1 | 1/2002 | Augustine et al. | |
| 6,374,827 B1 * | 4/2002 | Bowden et al. | 128/207.14 |
| 6,378,521 B1 | 4/2002 | Van Den Berg | |
| 6,386,199 B1 | 5/2002 | Alfery | |
| 6,390,093 B1 | 5/2002 | Mongeon | |
| 6,422,239 B1 | 7/2002 | Cook | |
| 6,427,686 B2 | 8/2002 | Augustine et al. | |
| 6,443,156 B1 | 9/2002 | Niklason et al. | |
| 6,450,164 B1 | 9/2002 | Banner et al. | |
| 6,460,540 B1 * | 10/2002 | Klepper | 128/207.14 |
| 6,604,525 B2 | 8/2003 | Pagan | |
| 6,612,305 B2 | 9/2003 | Fauza | |
| 6,631,720 B1 * | 10/2003 | Brain | 128/207.14 |
| 6,634,354 B2 | 10/2003 | Christopher | |
| 6,668,821 B2 | 12/2003 | Christopher | |
| 6,698,430 B2 | 3/2004 | Van Landuyt | |
| 6,705,318 B1 | 3/2004 | Brain | |
| 6,705,320 B1 | 3/2004 | Anderson | |
| 6,705,321 B2 | 3/2004 | Cook | |
| 6,705,322 B2 | 3/2004 | Chang | |
| 6,729,325 B2 | 5/2004 | Alfery | |
| 6,761,170 B2 | 7/2004 | Van Landuyt | |
| 6,799,574 B1 | 10/2004 | Collins | |
| 6,830,049 B2 | 12/2004 | Augustine et al. | |
| 6,892,731 B2 | 5/2005 | Cook | |
| 6,895,966 B2 | 5/2005 | Christopher | |
| 6,899,147 B2 | 5/2005 | Ogawa et al. | |
| 6,923,176 B2 * | 8/2005 | Ranzinger | 128/200.26 |
| 6,935,153 B2 | 8/2005 | Frigo et al. | |
| 6,983,744 B2 | 1/2006 | Alfery | |
| 6,986,755 B2 | 1/2006 | Willy et al. | |
| 7,013,899 B2 | 3/2006 | Alfery | |
| 7,021,686 B2 | 4/2006 | Glasgow et al. | |
| 7,040,312 B2 | 5/2006 | Alfery et al. | |
| 7,040,322 B2 | 5/2006 | Fortuna | |
| 7,052,456 B2 | 5/2006 | Simon | |
| 7,096,868 B2 | 8/2006 | Tateo et al. | |
| 7,097,802 B2 | 8/2006 | Brain | |
| 7,128,071 B2 * | 10/2006 | Brain | 128/207.15 |
| 2001/0050082 A1 | 12/2001 | Christopher | |
| 2004/0020491 A1 * | 2/2004 | Fortuna | 128/207.15 |
| 2004/0079364 A1 | 4/2004 | Christopher | |
| 2005/0016529 A1 | 1/2005 | Cook | |
| 2005/0051173 A1 | 3/2005 | Brain | |
| 2005/0139220 A1 | 6/2005 | Christopher | |
| 2006/0027238 A1 | 2/2006 | Lin | |
| 2006/0076021 A1 | 4/2006 | Chang | |
| 2006/0180156 A1 | 8/2006 | Baska | |
| 2006/0207597 A1 * | 9/2006 | Wright | 128/206.11 |
| 2007/0028923 A1 | 2/2007 | Souris et al. | |
| 2007/0102001 A1 | 5/2007 | Brain | |
| 2007/0137651 A1 | 6/2007 | Glassenberg et al. | |
| 2007/0246050 A1 | 10/2007 | Parikh et al. | |
| 2008/0078398 A1 | 4/2008 | Cook | |

OTHER PUBLICATIONS

"Arndt Endobronchial Blocker Set," www.cookcriticalcare.com, undated.

"Products—LMA Fastrach," http://www.lmana.com/prod/components/products/lma_fastrach.html, printed on Jun. 19, 2005, one page.

"9c Removal of LMA-Fastrach Prior to Extubation," LMA-Fastrach Instructional Manual, www.lmana.com/docs/fastrach_instruction.pdf, Feb. 2002, pages cover (2 pages), 26-27.

Byrd, Jr., R.P."Ventilation, Mechanical," http://www.emedicine.com/med/topic3370.htm, Jul. 6, 2006, pp. 1-13.

"Ambu Product Information," Ambu A/S, 2007, pp. 1-18, Denmark.

"Intersurgical Complete Respiratory Systems," http://www.intersurgical.com/productscatalog/choosegroup.aspx?cm..., printed on Apr. 11, 2007, one page.

"LMA Airway Instruction Manual," The Laryngeal Mask Company Limited, www.lmana.com/docs/LMA_Airways_Manual.pdf, 2005, pp. 1-23.

International Search Report, International Patent Application No. PCT/US2008/060425, mailed Sep. 29, 2008, 11 pages.

* cited by examiner

LARYNGEAL MASK WITH ESOPHAGEAL BLOCKER AND BITE BLOCK

BACKGROUND

1. Field of the Invention

The invention relates to an artificial airway device more specifically to a supraglottic airway designed to guide an esophageal blocker device into the esophagus and including a bite block.

2. Description of the Related Art

In general, supraglottic airways such as laryngeal masks allowing for both rapid lung ventilation and the insertion of medical instruments and tubes into the laryngeal openings of patients have been described in patents, such as U.S. Pat. No. 4,509,514 to Brain and U.S. Pat. Nos. 6,422,239 and 5,937,860 to Cook the entire disclosures of which were herein incorporated by reference. Laryngeal masks generally consist of two major components, a breathing tube and an inflatable mask, these devices are inserted into a patient's throat, and when properly positioned, cover the laryngeal opening. A seal is then formed around the circumference of the laryngeal opening by the inflation of a ring-like structure located toward the front of the mask (patient end). Inflation of the ring exerts pressure against the front, sides, and rear portions of the oropharynx, securing the device in place such that the laryngeal opening is positioned in alignment with a recessed cavity in the mask face. Extending from a point external to the oral cavity, the flexible breathing tube terminates within the recessed cavity, aligned axially with the laryngeal opening. The positioning of the flexible breathing tube allows the passage of endo-tracheal tubes or related medical instruments into the laryngeal opening, in addition to allowing for lung ventilation.

While current supraglottic airways such as laryngeal masks can provide for improved placement and breathing over a traditional endotracheal tube, they can still be improved. It has recently been recognized that it is desirable to both block off the patient's esophagus during use of the supraglottic airway to prevent stomach contents from interfering with the supraglottic airway and to prevent a patient's unintentional biting behavior from interfering with air passage in the supraglottic airway. Such blocking is not intended to inhibit movement of stomach contents during violent muscle contractions (such as while vomiting) but to inhibit more passive movement. Still further, it has been recognized that many patients who need a supraglottic airway have lost muscle control and can involuntarily bite down on the breathing tube which can result in it becoming obstructed and causing the patient discomfort and placing them in danger of potential suffocation.

SUMMARY

Because of these and other problems in the art described herein is a supraglottic airway primarily intended to facilitate lung ventilation and the insertion of endo-tracheal tubes or related medical instruments into a patient's trachea as needed during general anesthesia, intensive care, critical patient care, or at any other time that ventilation would be desired. In a laryngeal mask embodiment of such a supraglottic airway, the mask comprises a flexible ventilation tube and an inflatable positioning shield generally conforming to the anatomy of the oropharynx region surrounding the laryngeal opening, and securely affixed to the distal end of the ventilation tube. The airway also includes an esophageal blocker and a guide structure for guiding the esophageal blocker into the esophagus, the blocker being deployed to block off the esophagus below the airway after the airway has been inserted. The airway additionally or alternatively includes a bite block designed to inhibit the patient from biting the breathing tube closed while the airway is in use.

There is described herein, among other things, a supraglottic airway and esophageal blocker in combination comprising; an esophageal blocker; a supraglottic airway including: a respiratory tube; means for creating an airtight seal in the oropharyngeal region of a patient; and a guide structure capable of guiding said esophageal blocker into an esophagus of said patient; wherein, when said airway is in said patient, said esophageal blocker can move relative to the airway and can be extended through said guide structure to then extend past a distal end of said airway into said esophagus of said patient.

In an embodiment of the combination the esophageal blocker is transported by said guide structure as said airway is placed in said patient. The guide structure may comprise a secondary tube which may be slotted.

In an embodiment, the respiratory tube is smoothly curved, the guide structure is mounted to said respiratory tube, and the airway includes a clip for holding said esophageal blocker in position relative said airway.

In an embodiment, the esophageal blocker includes an inflating and positioning tube and a balloon. The inflating and positioning tube may include markings to identify the location of said balloon relative said airway.

In a still further embodiment, the combination further comprises: a bite block formed onto said respiratory tube, wherein said bite block is sized and shaped to contact at least a portion of the teeth of a patient, when said airway is in said patient, if said patient attempts to bite down on said respiratory tube.

There is also described herein, a laryngeal mask and esophageal blocker in combination comprising; an esophageal blocker; a laryngeal mask including: a respiratory tube; a shield comprising an inflatable outer ring and a posterior base; and a guide structure capable of guiding said esophageal blocker into an esophagus of a patient; wherein, when said laryngeal mask is in said patient, said esophageal blocker can move relative to said mask and can be extended through said guide structure to then extend past a distal end of said shield into said esophagus of said patient.

In an embodiment of the combination the esophageal blocker is transported by said guide structure as said mask is placed in said patient. The guide structure may comprise a secondary tube which may be slotted.

In an embodiment of the combination the secondary tube is not directly connected to said shield. However, the secondary tube may direct a distal end of said esophageal blocker along said shield when said esophageal blocker is extended into said esophagus of said patient. The distal end of said esophageal blocker passing along a line of connection formed by the intersection of said posterior base and said outer ring and passing between said shield and said patient's oropharynx at said distal end of said shield.

In an embodiment, the respiratory tube is smoothly curved, the secondary tube twisting at least partially around said respiratory tube.

In an embodiment, the esophageal blocker includes an inflating and positioning tube and a balloon. The inflating and positioning tube may include markings to identify the location of said balloon relative said mask.

In an embodiment of the combination, the guide structure is mounted to said respiratory tube or said shield, and the airway includes a clip for holding said esophageal blocker in position relative said mask.

In a still further embodiment, the combination further comprises: a bite block formed onto said respiratory tube; wherein said bite block is sized and shaped to contact at least a portion of the teeth of a patient, when said laryngeal mask is in said patient, if said patient attempts to bite down on said respiratory tube.

There is also described herein, a laryngeal mask including an esophageal blocker, the mask comprising; a respiratory tube; a shield comprising an inflatable outer ring and a posterior base; esophageal blocking means for temporarily blocking off a patient's esophagus; and a guide means mounted to said respiratory tube for guiding said esophageal blocking means into said esophagus below a distal end of said shield. The esophageal blocking means may be transported by said guide means as said laryngeal mask is placed in said patient.

There is also described herein, a method for blocking a patient's esophagus while providing them with an artificial airway, the method comprising the steps of: providing a supraglottic airway capable of creating an airtight seal in the oropharyngeal region of a patient; providing an esophageal blocker; placing said supraglottic airway in a patient in the oropharyngeal region of said patient to provide the patient with an artificial airway; moving said esophageal blocker relative to said supraglottic airway in such a manner that a portion of said esophageal blocker is guided by the structure of said supraglottic airway past said supraglottic airway and into the esophagus of said patient, deploying said esophageal blocker in said esophagus to block said patient's esophagus.

There is also described herein, a laryngeal mask including a bite block, the mask comprising: a respiratory tube having a hollow passageway there through; a shield comprising an inflatable outer ring and a posterior base; and a bite block formed onto said respiratory tube; wherein said bite block is sized and shaped to contact at least one of: the cuspids, the bicuspids, or the molars of the patient, when said laryngeal mask is in said patient, if said patient attempts to bite down on said respiratory tube, said bite block preventing said bite from completely closing said hollow passageway.

In an embodiment of the mask, the respiratory tube is curved. In another embodiment of the mask the bite block is located on a side of said respiratory tube and a second bite block may be arranged on the opposing side of said respiratory tube.

DESCRIPTION OF THE PREFERRED EMBODIMENT(S)

Figure 1:
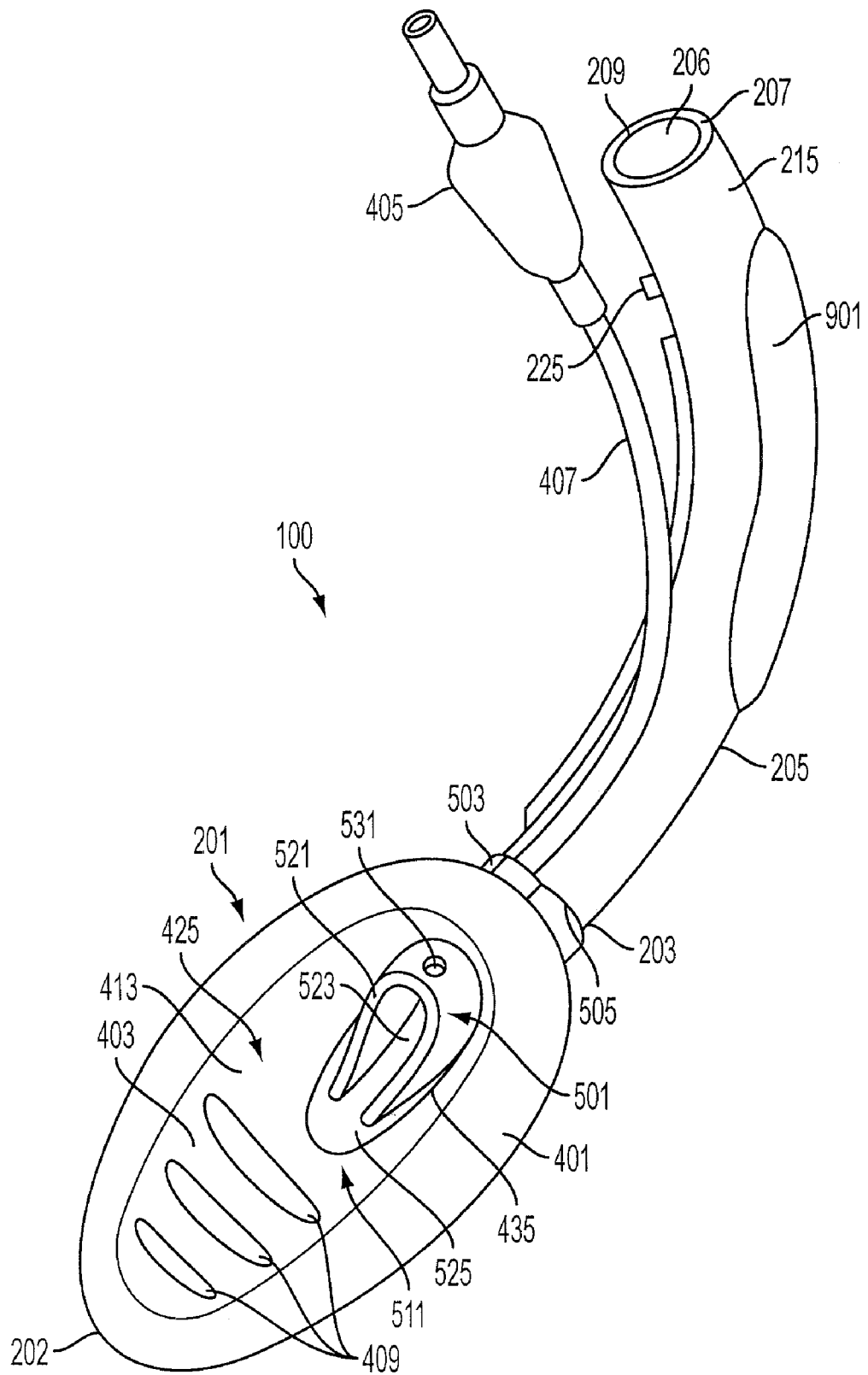
FIG. 1 shows a perspective view of an embodiment of a laryngeal mask including a transport tube for an esophageal blocker and a bite bock.
Figure 2:
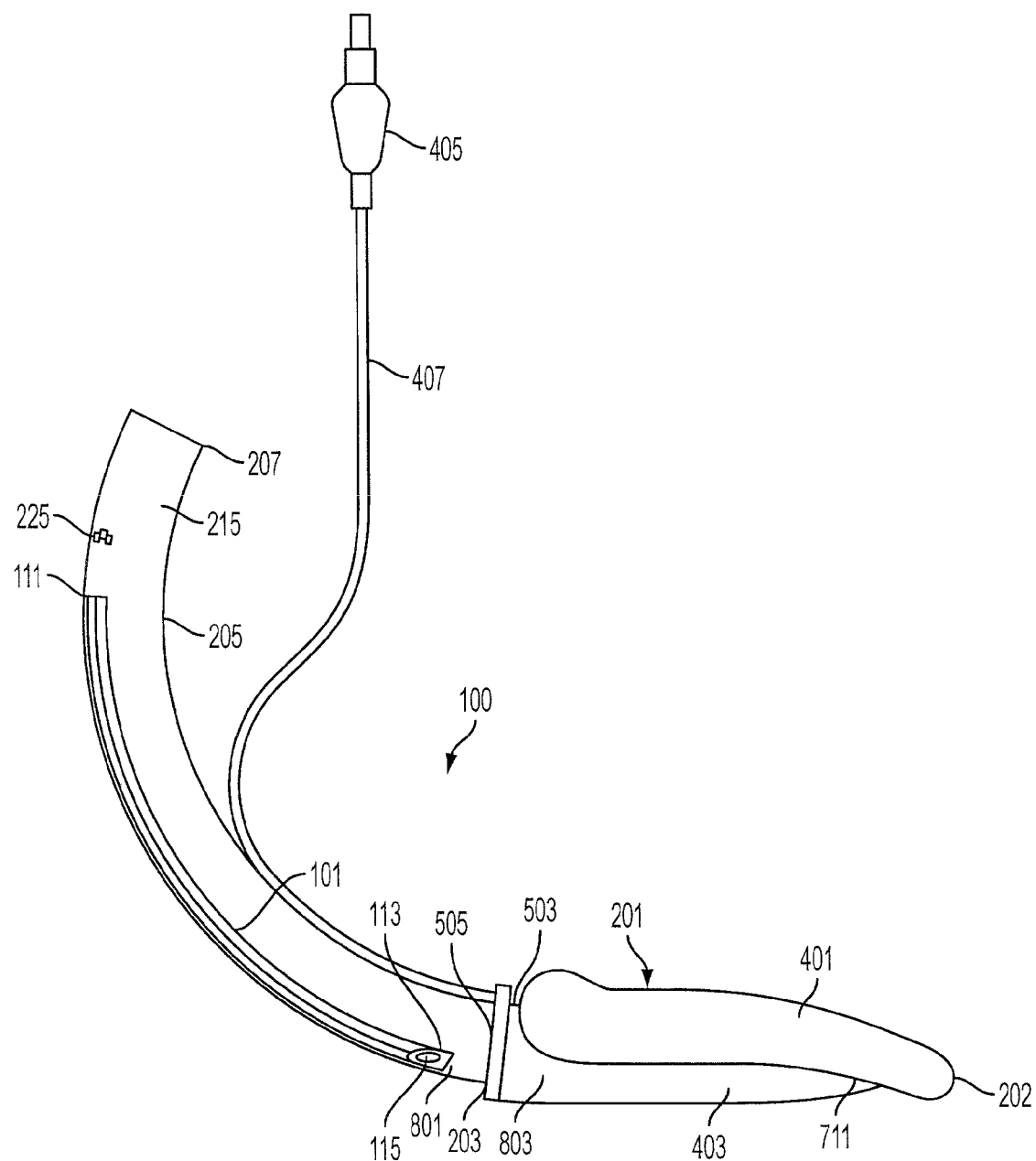
FIG. 2 shows a right side view of the embodiment of FIG. 1.
Figure 3:
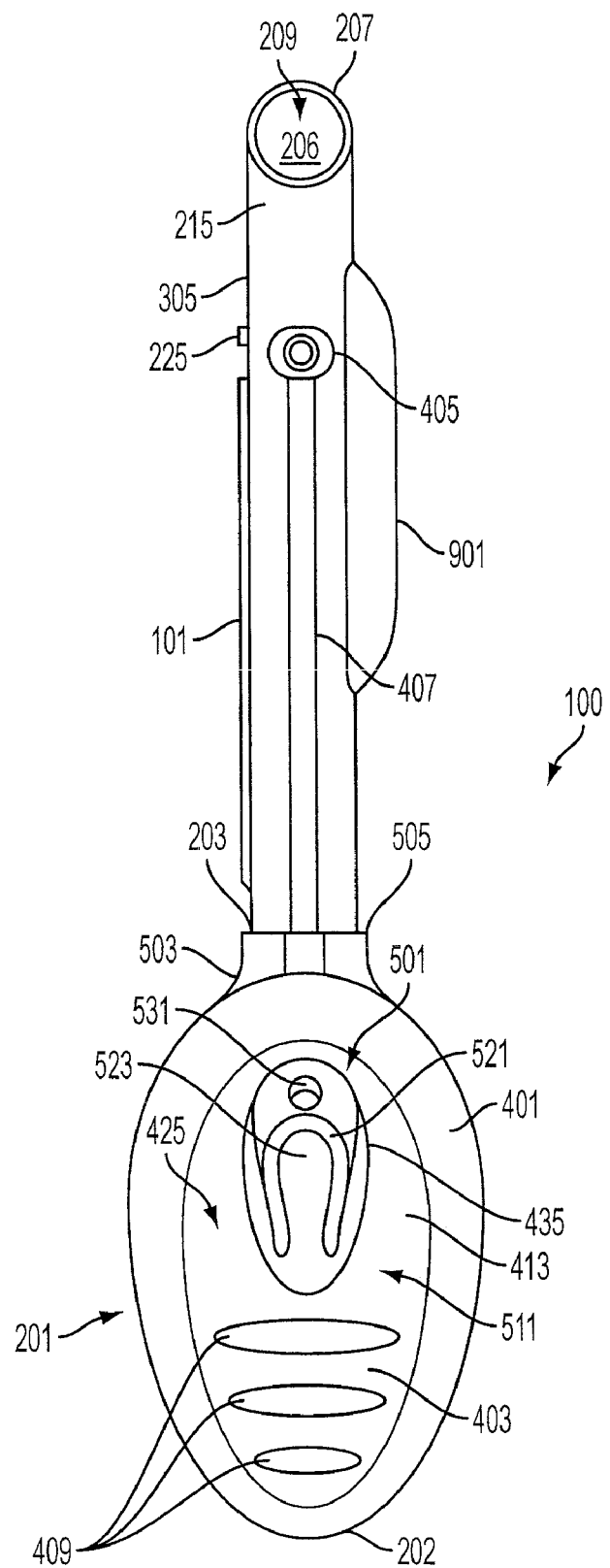
FIG. 3 shows a top view of the embodiment of FIG. 1.
Figure 4:
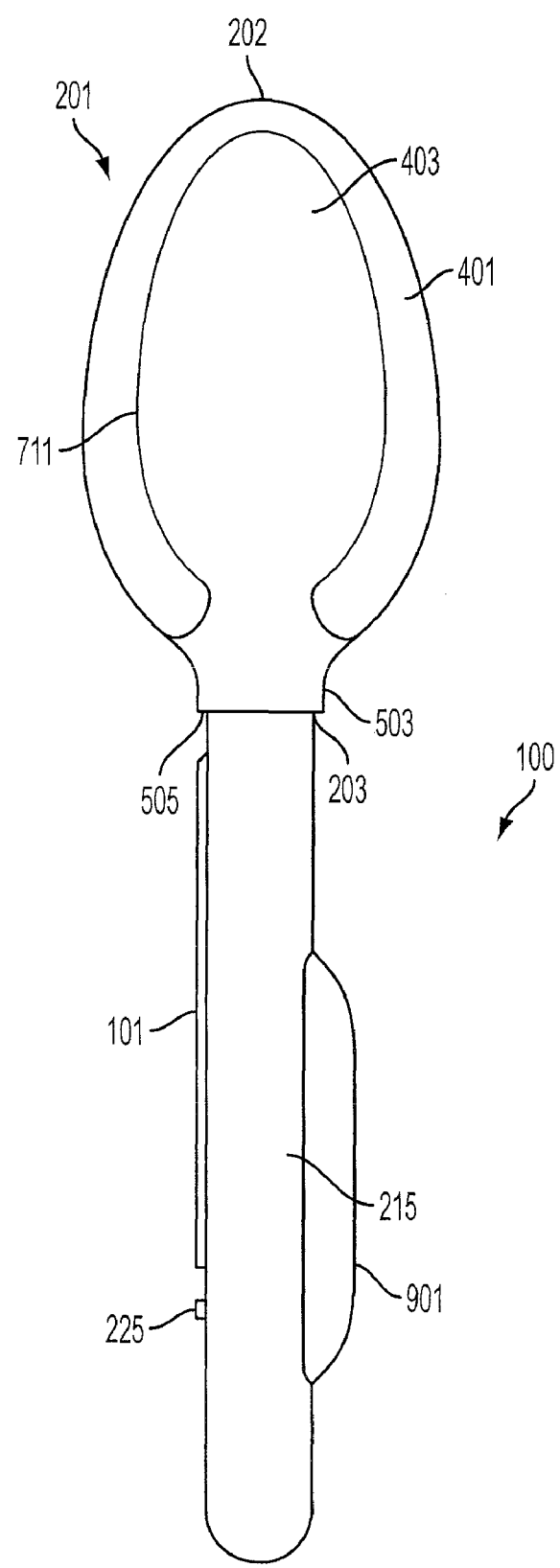
FIG. 4 shows a bottom view of the embodiment of FIG. 1.
Figure 5:
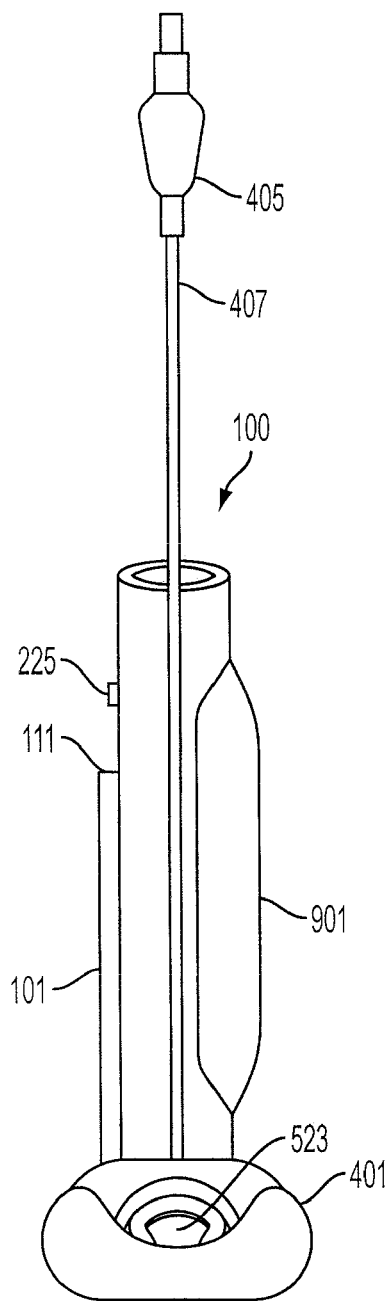
FIG. 5 shows a front view of the embodiment of FIG. 1.
Figure 6:
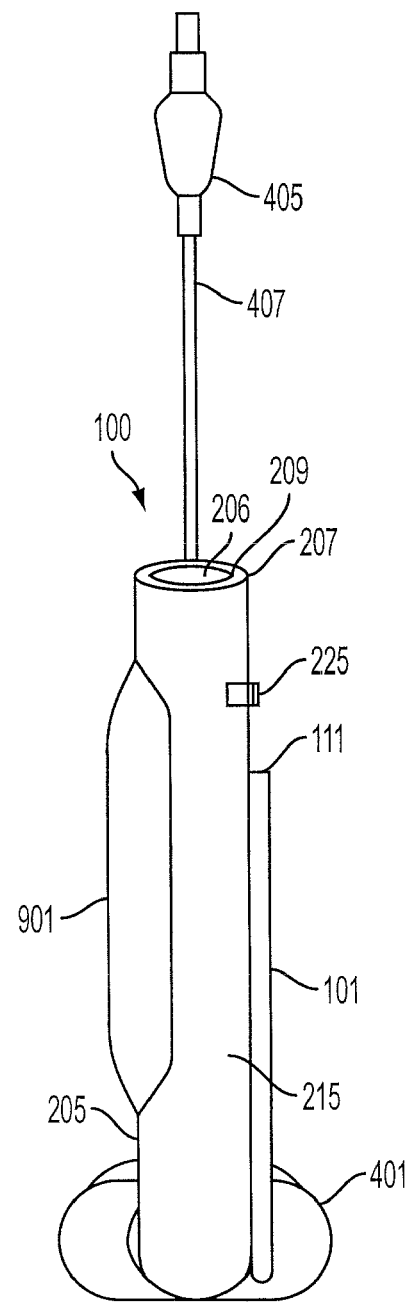
FIG. 6 shows a rear view of the embodiment of FIG. 1

The following detailed description illustrates by way of example and not by way of limitation. Described herein, among other things, is an embodiment of a supraglottic airway which is designed for use with an esophageal blocker. Specifically, the supraglottic airway includes structures which enable the airway to transport an esophageal blocker into the oropharynx area when the airway is inserted, and then facilitate the deployment of the esophageal blocker into the esophagus either during placement or once the airway is positioned. While the supraglottic airway described herein incorporates certain features for improved placement in the airway, it should be recognized that these features are not required for use of the esophageal blocker and the esophageal blocker and associated components attached to the airway can be used on any form of supraglottic airway.

FIGS. 1-6 provide for an embodiment of a supraglottic airway in the form of removable laryngeal mask airway (100). The mask (100) is chosen as an exemplary form of supraglottic airway which may be used in conjunction with the esophageal blocker to simply demonstrate how the systems and methods of esophageal blocking in conjunction with an airway can operate. It is in no way intended to be descriptive of all airways which may be used in other embodiments. The mask (100) includes a guide structure for use with a esophageal blocker (801) and a bite block (901). In the depicted embodiment, the laryngeal mask (100) generally comprises two major components. There is an inflatable positioning shield (201) secured toward the distal end (203) of a respiratory tube (205) which is formed into an arcuate curve. The inflatable positioning shield (201) is composed of a soft flexible material such as, but not limited to, silicone-rubber polymer.

The inflatable positioning shield (201) is composed of a generally wedge-shaped ellipsoid, ovoid, or toroid outer ring (401) with a pliable molded posterior base (403) attached thereto. The outer ring (401) is preferably repeatedly inflatable and deflatable with such inflation being accomplished by attachment of an inflation device (405) which is capable of pulling air from the ambient, into an inflation tube (407) and from there into the interior of the outer ring (401). The outer ring (401), when inflated, is sized and shaped to generally conform to the approximate available space in the oropharynx region.

The posterior base (403) is secured longitudinally within the hole in the center of the outer ring (401). The posterior base (403) is generally attached in a fashion to form an elongated and tapered hemisphere relative the generally major plane of the outer ring (401) so as to give the shield (201) the overall shape as seen in the FIGS. In the depicted embodiment, there are semi-rigid raised ridges (409) positioned longitudinally parallel to each other along the surface (413) of the posterior base (403) "inside" the hole of the outer ring (401).

The shield (201) is generally connected to the respiratory tube (205) by means of a hollow wedge (501) which allows the respiratory tube to pass through the shield (201) and into the recessed cavity (511) formed above the posterior base (403) and inside the hole in the outer ring (401).

The hollow wedge (501) is attached generally to the distal end (203) of the respiratory tube (205) which has passed through an airtight peripheral seal (505) towards the rear (503) of the inflatable positioning shield (201). The wedge (501) therefore gives an access into the shield recess (511) from the interior of the respiratory tube (205) allowing air to pass from the recessed cavity (511) into the distal end (203) of the respiratory tube (205) and from there out the proximal end (207) of the respiratory tube (205). The wedge (501) is generally formed into an angle (521) to the length of the respiratory tube (205) which is generally between 0 and 90 degrees and preferably about 30 to about 35 degrees with the posterior base (403), forming an elongated elliptically shaped distal lumen (523) open to the interior of the shield recess (511) and interior of the respiratory tube (205). The elongated lower surface of the wedge will generally comprise a reinforced support (525) which is affixed to the posterior base (403) possibly in a similarly sized recess (435) in said posterior base (403). The connection between the posterior base (403) and the reinforced support (525) may be formed in any manner known to one of ordinary skill in the art, however, in a preferred embodiment, the two devices are adhered together with a generally non-separable adhesive. In an alternative embodiment, they may be co-formed. The wedge (501) and respiratory tube (205) generally pass through the shield (201) in such a fashion as to form an airtight seal which inhibits air in the shield (201) from entering the respiratory tube (205) and vice-versa.

There may also be included a ventilation lumen (531) through the wedge (501) to provide an alternate airway in the event the distal lumen (523) becomes obstructed during patient lung ventilation. The ventilation lumen (531) also generally prevents the formation of a pressure differential between the shield recess (425) and flexible respiratory tube (205). Absent a pressure differential, any object obstructing the distal lumen (523) will not generally become inextricably lodged.

This general type of shield (201) is generally used on a number of different laryngeal masks (100) with modification of the shapes and sizes of various components. However, those of ordinary skill in the art will recognize that there is no need to include the shield (201) in other forms of supraglottic airway and that the seal to be generated with the pharynx can be generated in alternative fashions. In particular, other embodiments of airways can include alternative or additional structures for providing the airway. In other embodiments, the supraglottic airway, instead of providing a shield (201) may alternative provide another structure for creating a generally airtight seal in the oropharyngeal region of a patient, such as, but not limited to, an inflatable cuff, a solid structure sized and shaped to form such a seal with the oropharyngeal region by interaction with the throat, a structure capable of being held in place by positive or negative pressure, or any other structure or structures understood by one of ordinary skill in the art.

The respiratory tube (205) may be formed in any manner known to those of ordinary skill in the art but will generally form a smoothly curving hollow cylinder of generally circular or elliptical cross-section preferably approximating, for ease of insertion, the shape of the human throat. The respiratory tube (205) is preferably sized and shaped to accommodate the passage of endo-tracheal tubes and related medical devices up to 8.5 French in diameter. The length of respiratory tube (205) is such that when the laryngeal mask (100) is properly positioned for use within the oropharynx, the attachment (proximal) end (207) of respiratory tube (205) is located exterior to the oral cavity of the patient. The attachment end (207) of the respiratory tube (205) terminates in an unobstructed proximal lumen (209), providing a direct pathway through the respiratory tube (205) to the distal end (203) and distal lumen (523). In alternative embodiments, the attachment end (207) may be fitted with adapters or connectors (not shown) suitable for connection to a variety of medical devices, for example, lung ventilation machines.

There is also shown attached to the respiratory tube (205) a guide structure which in the depicted embodiment comprises a slotted secondary tube (101) which is placed externally to the respiratory tube (205) and runs generally along the outer surface (215) of the respiratory tube (205) in a curving pattern such as a partial helix. As can be seen in the FIGS, the secondary tube (101) is generally placed so as to have its proximal end (111) toward the proximal end (2.07) of the respiratory tube (205) and its distal end (113) toward the distal end (203) of the respiratory tube (205) prior to the airtight peripheral seal (505).

The secondary tube (101) is also preferably positioned so that its proximal end (111) is located on the side of the respiratory tube (205) relative to its curve as shown in the FIGS. This means the proximal end (111) of the secondary tube (101) is generally located at a point generally spaced at about its maximum from the plane which incorporates the curve of the respiratory tube (205) and that passes through the center of the respiratory tube (205). The secondary tube (101) then runs along the outside of the respiratory tube (205) generally twisting slightly about the outer surface (215) of the respiratory tube (205) so as to terminate at its distal end (113) at a point closer to the plane discussed above than the proximal end (111). That is, as shown in the FIG. 7, the proximal end (111) of the secondary tube (101) is located generally on the side of the respiratory tube (205) while the distal end (113) is generally arranged more toward the undersurface the respiratory tube (205).

Figure 10:
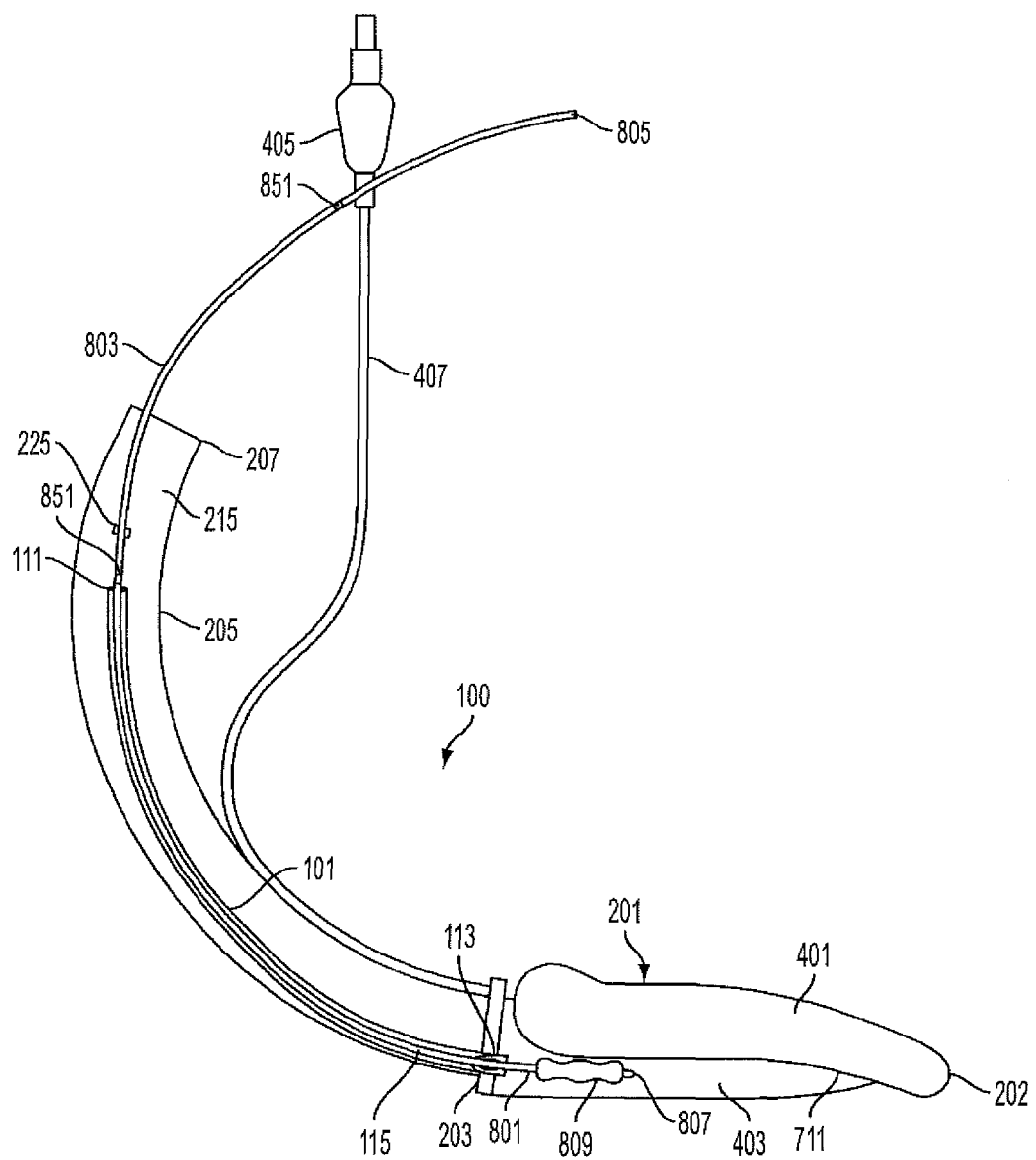
FIG. 10 shows an embodiment of a laryngeal mask including a transport tube for an esophageal blocker and bite block in which a slotted secondary tube is twisting partially around the respiratory tube.

Generally, the distal end (113) of the secondary tube (101) is positioned below the major plane of the shield (201) but is on the respiratory tube (205) and spaced from the peripheral seal (403) so that its structure is connected only to the respiratory tube (205). However, in alternative embodiments the guide structure may be mounted on the respiratory tube (205), shield (201), both, or elsewhere on the laryngeal mask (100). One such embodiment where the guide structure is mounted on the shield (201) and respiratory tube (205) is shown in FIG. 10. The distal end (113) of the secondary tube (101) may terminate in a angle relative to its length so as to provide a second elliptical lumen (115).

It should be recognized that in alternative embodiments, it is not required for the guide structure to be a slotted tube as is depicted in FIGS. 1-6. In alternative embodiments, the guide structure may comprise a tube. Or alternatively may have a larger slit or opening along its length and form a trough type of shape. In a still further embodiment, the guide structure may comprise a series of small tubes or troughs with spaces between them which together serve as the guide structure. Generally, the guide structure may take virtually any shape or traverse the airway in any orientation instead being defined as being able to guide the inflation and positioning tube (803) of the blocker (801) along a predefined pathway when the blocker (801) is being installed in the patient.

Figure 7:
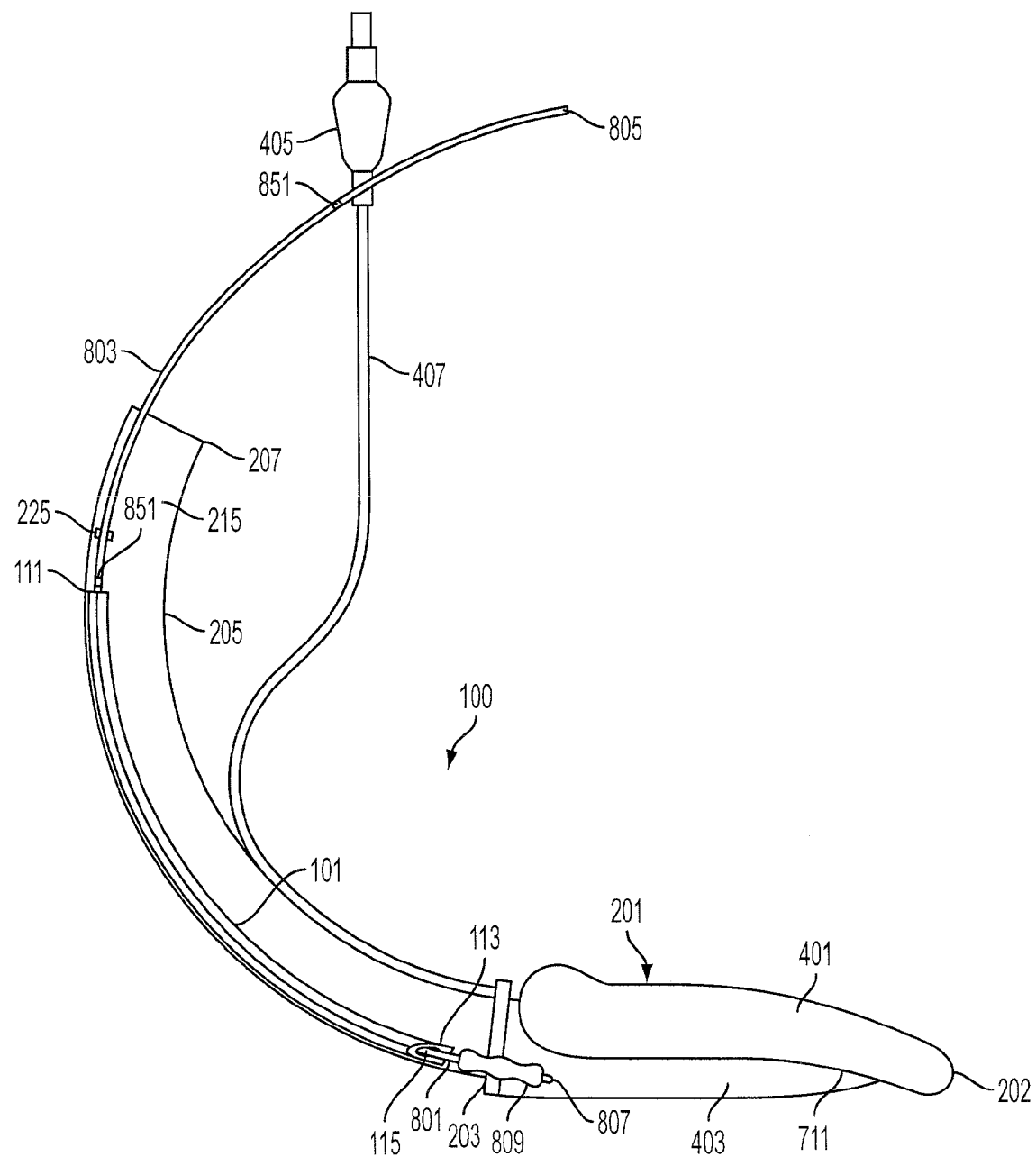
FIG. 7 shows the embodiment of FIG. 1 with an esophageal blocker in the ready position, as it preferably would be during insertion of the mask into a patient.
Figure 8:
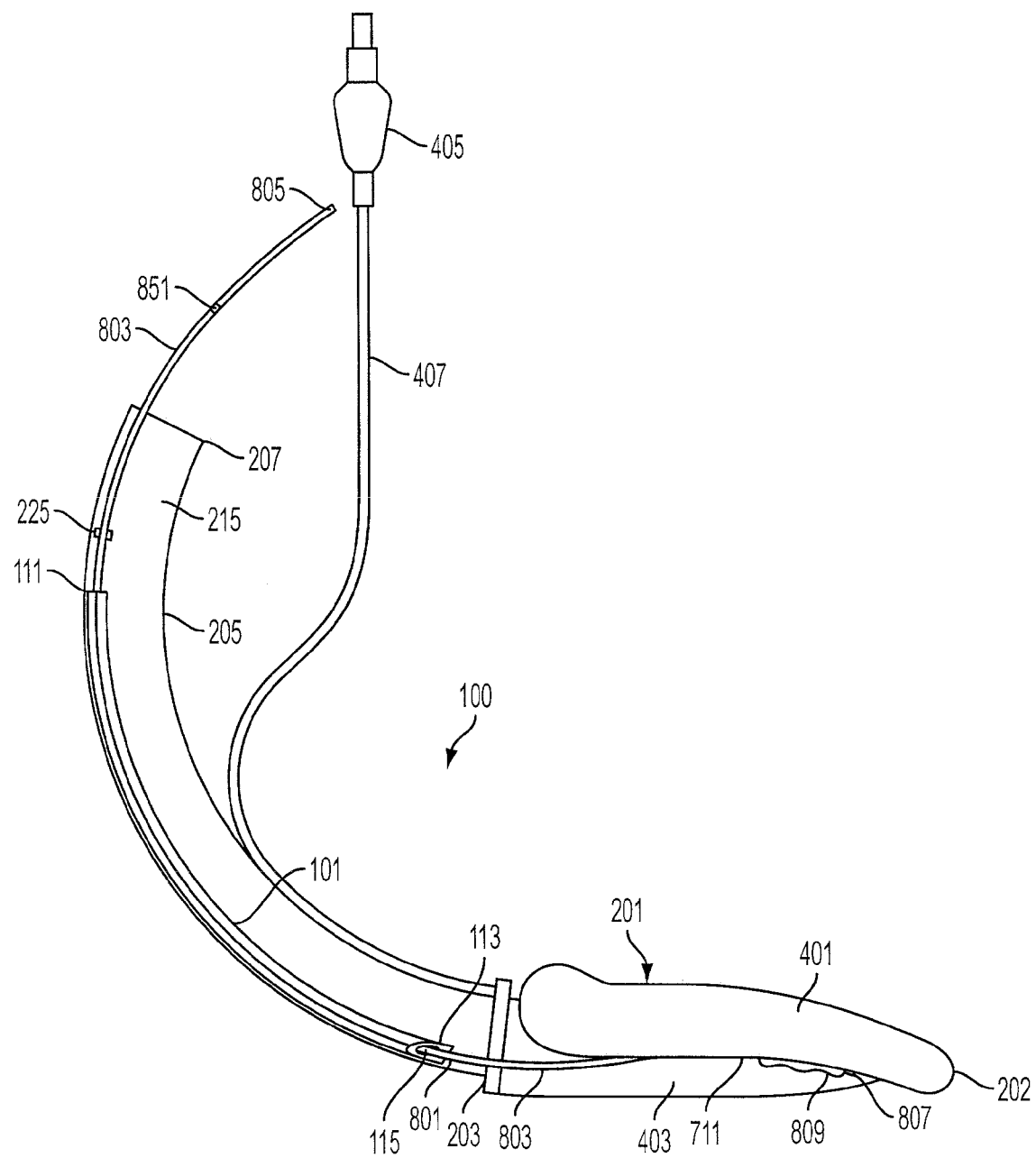
FIG. 8 shows the esophageal blocker of FIG. 5 as it is in the process of being deployed. The distal end of the blocker is shown tracking the void generally produced by the inter'section of the posterior base, the inflatable rim, and the patient's throat.

Supported by the guide structure is an esophageal blocker (801). In this case, the esophageal blocker (801) generally comprises an inflation and positioning tube (803) having a proximal (805) and distal (807) end and a length therebetween. Positioned toward or at the distal end (807) of the esophageal blocker (801) is a repeatedly inflatable and deflatable balloon (809) as is understood by those of ordinary skill in the art. In the depiction of FIGS. 7 & 8 the balloon (809) is in its deflated position, while in FIG. 9 the balloon (809) is in its inflated position.

The inflation and positioning tube (803) will generally comprise a hollow tube having a maximum external diameter smaller than the minimum internal diameter of the secondary tube (101) so as to allow the esophageal blocker (801) to pass through the secondary tube (101). This passage may be facilitated by the inclusion of lubricants on the exterior surface of the esophageal blocker (801) as is known to those of ordinary skill in the art.

In the depicted embodiment, there is also included on the exterior surface (215) of the respiratory tube (205) a retainer clip (225) which is generally positioned above the proximal end (111) of the secondary tube (101) and is sized and shaped to frictionally or otherwise secure the inflation and positioning tube (803) of the esophageal blocker (801). This clip (225) is used to hold the esophageal blocker (801) in a selected position relative to the respiratory tube (205) during insertion and deployment.

In the depicted embodiment, there is also included on the exterior surface (215) of the respiratory tube (205), a bite block (901). The bite block (901) generally comprises a solid structure generally comprised of a plastic or other material with a relatively high compression resistance such as, but not limited to, hard rubber. The bite block (901) runs generally down the opposing side of the respiratory tube (205) to the secondary tube (101) and along a proximal portion of the length of the respiratory tube (205). The length and extension from the respiratory tube (205) is preferably selected so that when the laryngeal mask (100) is placed within a human patient, the bite block (901) does not pass into the throat but is within the oral cavity and possibly extends beyond the oral cavity outside the body.

The bite block (901) is generally designed so as to resist deformation of itself and the respiratory tube (205) in the event that the person who has had the laryngeal mask (100) installed in the orolaryngeal region was to involuntarily or voluntarily bite down on the respiratory tube (205). In particular, to be sufficiently resistant to deformation that the patient would generally be unable to generate sufficient force from the bite to compress the respiratory tube (205) sufficiently to close off the hollow passageway (206) therethrough and prevent air from passing through it. While the bite block (901) is not intended to prevent all deformation of the respiratory tube (205), the bite block (901) is intended to inhibit the biting action from closing off the internal passageway through the respiratory tube (205) completely.

To achieve this, the bite block (901) will generally stick out a sufficient distance from the exterior surface (215) of the respiratory tube (205) to be between the cuspids, bicuspids, or molars in the oral cavity of the person who has had the laryngeal mask (100) placed in their oropharyngeal region. In particular, using the ADA "Current Dental Terminology, 3rd edition (CDT-3) © 1999 Universal/National System of tooth numbering, the bite block will preferably contact at least one tooth of number 1 through 6, 10 through 22, or 28 through 32 in permanent dentition or of letter A through C, H through M, or R through T in primary dentition. In this way, their biting action is inhibited because the bite block (901) is located between the premolar's and molars on at least one side of the mouth. This makes it difficult for a biting action, to close the front teeth sufficiently to block the respiratory tube (205) when the bite block (901) is between these rearward teeth on either or both sides of the mouth. Even if significant force is placed on the bite block (901), the positioning of the bite block (901) between these teeth will generally prevent the front teeth from closing sufficiently to seal off the internal opening of the respiratory tube (205) as it leaves the mouth.

In this embodiment, the bite block (901) is generally hemispherical mirroring the size and shape of the respiratory tube (205). This shape both inhibits deformation and presents generally smooth surfaces to the interior of the mouth to inhibit injury from biting on the bite block (901) and to give a large surface for contact with the teeth.

While the embodiment of the laryngeal mask (100) in the FIGS shows both a bite block (901) and an esophageal blocker (801), one of ordinary skill would understand that in other embodiments a supraglottic airway could have only one or the other structure depending on the needs of the individual using it. In particular, in an embodiment, the supraglottic airway includes a bite block (901) but not a guide structure or esophageal blocker (801), and in another embodiment, the airway includes the guide structure and the esophageal blocker (801) but not the bite block (901). In a still further embodiment, a bite block (901) can be placed on both sides of the airway so as to provide for potentially easier placement and further inhibition on the effects of biting.

Generally, use of the laryngeal mask (100) would proceed as follows. The mask (100) is first placed in the ready position of FIG. 7. In this situation, the outer ring (401) may be inflated, partially inflated, or fully deflated, and the esophageal blocker (801) is located in the secondary tube (101) with its distal end (807) within or near the distal end (113) of the secondary tube (101) and the balloon (809) deflated. The inflation and positioning tube (803) of the esophageal blocker (801) is also secured in the clip (225) to inhibit a change in position. The mouth of the patient is opened and their head positioned for insertion of the mask (100). The outer ring (401) is pushed into the orolaryngeal region. The smooth arcuate curve of the combined respiratory tube (205) and shield (201) positions the laryngeal mask (100) in alignment with the laryngeal opening. Upon proper positioning, as generally determined by a resistance to further forward motion, the outer ring (401) is inflated using the inflation device (405). When fully inflated, the outer ring (401) exerts sufficient pressure against the structures of the oropharynx to form a tight seal surrounding the laryngeal opening.

Positioned within the recessed cavity (511), the distal lumen (523) is axially aligned with the laryngeal opening, permitting positive lung ventilation to be performed, or allowing endo-tracheal tubes or related medical instruments inserted through the respiratory tube (205) to exit through the distal lumen (523) which is directly aligned for passage into the laryngeal opening. The bite block (901) is also aligned between the molars.

Once the laryngeal mask (100) is thus aligned, the user will unclip the inflation and positioning tube (803) of the esophageal blocker (801) from the clip (225) which will allow for movement of the esophageal blocker (801) relative to the mask (100). In an alternative embodiment, mask (100) does not carry the esophageal blocker (801) during insertion. Instead, the esophageal blocker (801) is inserted into the guide structure once the mask (100) is in place in the patient. In either case, the user will advance the distal end (807) of the esophageal blocker (801) toward the shield (201). Because of the inflation of the outer ring (401), there will generally be a roughly triangular cross-sectioned, funnel-shaped void formed at the line of connection (711) of the outer ring (401) and the posterior base (403) and the interaction of these devices with the rear of the patient's oropharynx. As the distal end (807) of the esophageal blocker (801) is extended, it is naturally directed into this void and runs generally along the intersection of the outer ring (401) and posterior base (403) as shown in FIG. 8. As this void is a generally smooth funnel-shaped curve having relatively low curvature, the distal end (807) generally tracks along the line of connection (711) and is held in proximity to the line of connection (711) by the throat.

As should be apparent, the prior inflation or partial inflation of the outer ring (401) has pressed the material of the outer ring (401) in fairly tight contact with the throat. As the distal end (807) approaches the distal end (202) of the shield (201), the curvature of the line of connection (711) will begin to increase at a dramatic rate. Further, the outer ring (401) generally presents less pressure against the back of the throat here. The continued forward force on the esophageal blocker (801) from the user advancing it through the secondary tube (101) will result in the distal end (807) attempting to continue around the tightening curve, however the inherent stiffness of the inflation and positioning tube (803) will inhibit it bending at a sufficient curvature to continue to follow the line of connection (711) and the distal end (807) will eventually "jump" the line of connection (711) and pass between the outer ring (401) and the posterior pharynx toward the distal end (202) of the shield (201).

Figure 9:
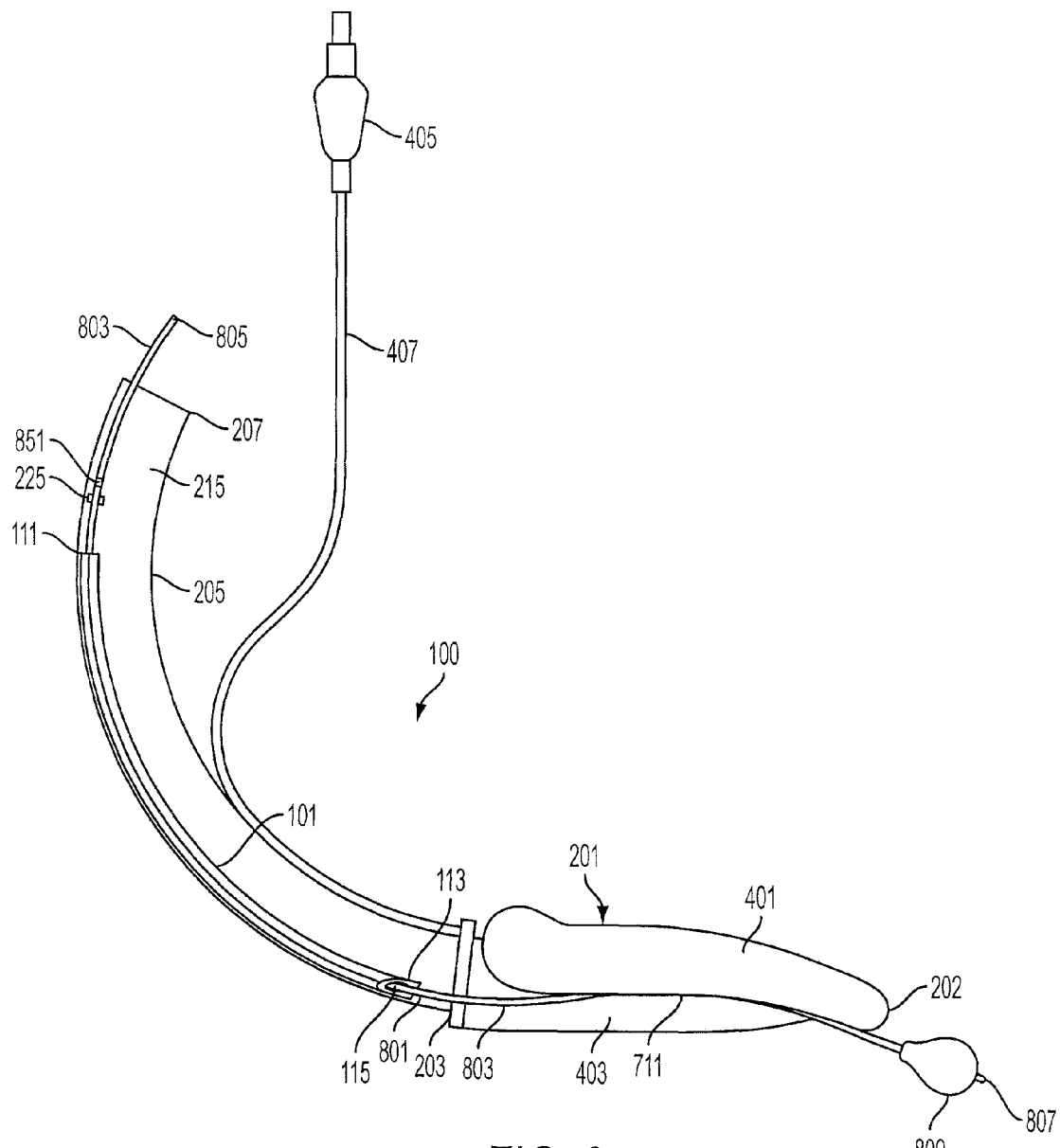
FIG. 9 shows the esophageal blocker of FIG. 5 in the deployed position with the balloon of the blocker inflated.

As should be apparent from FIG. 9, this point of jumping has the inflation and positioning tube (803) aligned with the esophagus as the line of connection (711) between the outer ring (401) and proximal base (403) over most of the transversed distance is generally in line with the esophagus. Further, the shield (201) is located between the laryngeal opening and the esophageal blocker (801), and has generally sealed off the laryngeal opening from the esophagus by the inflation of the outer ring (401).

Once the distal end (807) of the esophageal blocker (801) has jumped the line of connection (711) and passed between the outer ring (401) and the posterior pharynx, the inflation and positioning tube (801) will then generally be advanced a certain additional distance beyond the distal end (202) of the shield (201) and into the proximal esophagus at which time the inflation and positioning tube (803) is re-secured to the clip (225) to hold the blocker (801) in the desired deployment position. The balloon (809) is then inflated in the esophagus producing the layout shown in FIG. 9.

The blocking of the esophagus can be useful in the prevention of stomach gases or contents from coming up toward the laryngeal mask (100) and either interfering with its operation, causing damage, or injuring the patient. While it is not presumed that the esophageal blocker (801) will be sufficient to prevent the expelling of the mask (100) from a particularly strong muscle contraction (such as occurs when vomiting), it will generally prevent weaker movement of stomach contents (such as from acid reflux disease) from interfering with its operation.

In order to know the position of the esophageal blocker (801), the inflation and positioning tube (803) may have markings (851) thereon which generally correspond to the point at which the inflation and positioning tube (803) is to be clipped to the clip (225) to place the esophageal blocker (801) at both the ready position (FIG. 7) and the deployed position (FIG. 9). In this way, there is no guesswork as to the correct positioning. As should be apparent, in an alternative embodiment, the esophageal blocker (801) could be introduced into the secondary tube (101) once the mask (100) is already in place in the patient, and then threaded through to the deployed position. Further in some embodiments the clip (225) may be unnecessary to hold the esophageal blocker (801) in position.

As should be apparent from the FIGS., as the esophageal blocker (801) generally runs along the back of the shield (201) when moving from the original ready position to the deployed position, and the shield (201) is preferably secured over the laryngeal opening at the time of esophageal blocker (801) deployment, it is very unlikely that the esophageal blocker (801) could enter the lungs. To do so, it would have to pass around the mask (100) or through the shield (201), both of which actions are very unlikely. Instead, it is simply and preferentially deployed into the esophagus. Further, the shield (201) being placed against the major nerves near the larynx, also serves to shield them from the passage of the esophageal blocker (801) further helping to inhibit injury to the patient.

Removal of the laryngeal mask (100) and blocker is normally the reverse of the insertion procedure described above although the esophageal blocker (801) may be totally removed from the patient and the guide structure prior to removal of the mask (100) instead of simply returning it to the ready position.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A supraglottic airway and esophageal blocker in combination comprising;
   an esophageal blocker;
   a supraglottic airway including:
      a respiratory tube;
      a shield comprising a means for creating an airtight seal in the oropharyngeal region of a patient; and
      a guide structure external to said respiratory tube and said means; said guide structure being capable of guiding said esophageal blocker into an esophagus of said patient; said guide structure is not directly connected to said shield;
   wherein, while said supraglottic airway is inserted in said patient, said esophageal blocker can move relative to said supraglottic airway and can be extended through said guide structure to then extend past a distal end of said supraglottic airway into said esophagus of said patient.

2. The combination of claim 1 wherein said esophageal blocker is transported by said guide structure as said airway is placed in said patient.

3. The combination of claim 1 wherein said guide structure comprises a secondary tube.

4. The combination of claim 3 wherein said secondary tube is slotted.

5. The combination of claim 1 wherein said respiratory tube is smoothly curved.

6. The combination of claim 1 wherein said guide structure is mounted to said respiratory tube.

7. The combination of claim 1 wherein said airway further includes a clip for holding said esophageal blocker in position relative said airway.

8. The combination of claim 1 wherein said esophageal blocker includes an inflating and positioning tube and a balloon.

9. The combination of claim 8 wherein said inflating and positioning tube includes markings to identify the location of said balloon relative said airway.

10. The combination of claim 1 further comprising:
    a bite block formed onto said respiratory tube;

wherein said bite block is sized and shaped to contact at least a portion of the teeth of a patient, when said airway is in said patient, if said patient attempts to bite down on said respiratory tube.

11. A laryngeal mask and esophageal blocker in combination comprising;
an esophageal blocker;
a laryngeal mask including:
a respiratory tube;
a shield comprising an inflatable outer ring having a central hole attached to a posterior base, said central hole being in fluid communication with an interior of said respiratory tube; and
a guide structure external to said respiratory tube and said inflatable outer ring; said guide structure being capable of guiding said esophageal blocker into an esophagus of a patient; said guide structure is not directly connected to said shield;
wherein, after said laryngeal mask is inserted in said patient, said esophageal blocker can move relative to said mask and can be extended through said guide structure to then extend past a distal end of said shield into said esophagus of said patient.

12. The combination of claim 11 wherein said esophageal blocker is transported by said guide structure as said laryngeal mask is placed in said patient.

13. The combination of claim 11 wherein said guide structure comprises a secondary tube.

14. The combination of claim 13 wherein said secondary tube is slotted.

15. The combination of claim 13 wherein said secondary tube directs a distal end of said esophageal blocker along said shield when said esophageal blocker is extended into said esophagus of said patient.

16. The combination of claim 15 wherein said distal end of said esophageal blocker passes along a line of connection formed by the intersection of said posterior base and said outer ring.

17. The combination of claim 16 wherein said distal end of said esophageal blocker passes between said shield and said patient's oropharynx.

18. The combination of claim 17 wherein said distal end passes between said inflatable outer ring and said oropharynx at said distal end of said shield.

19. The combination of claim 13 wherein said respiratory tube is smoothly curved.

20. The combination of claim 19 wherein said secondary tube twists at least partially around said respiratory tube.

21. The combination of claim 11 wherein said guide structure is mounted to said respiratory tube.

22. The combination of claim 11 wherein said guide structure is mounted to said shield.

23. The combination of claim 11 wherein said mask further includes a clip for holding said esophageal blocker in position relative said laryngeal mask.

24. The combination of claim 11 wherein said esophageal blocker includes an inflating and positioning tube and a balloon.

25. The combination of claim 24 wherein said inflating and positioning tube includes markings to identify the location of said balloon relative said mask.

26. The combination of claim 11 further comprising:
a bite block formed onto said respiratory tube;
wherein said bite block is sized and shaped to contact at least a portion of the teeth of a patient, when said laryngeal mask is in said patient, if said patient attempts to bite down on said respiratory tube.

27. A laryngeal mask including an esophageal blocker, the mask comprising;
a respiratory tube;
a shield comprising an inflatable outer ring having a central hole attached to a posterior base, said central hole being in fluid communication with an interior of said respiratory tube;
esophageal blocking means for temporarily blocking off a patient's esophagus;
a guide means mounted externally to said respiratory tube for guiding said esophageal blocking means into said esophagus below a distal end of said shield; said guide structure is not directly connected to said shield;
wherein said esophageal blocking means is movable relative to said respiratory tube, said shield and said guide means.

28. The mask of claim 27 wherein said esophageal blocking means is transported by said guide means as said laryngeal mask is placed in said patient.

29. A method for blocking a patient's esophagus while providing said patient with an artificial airway, the method comprising the steps of:
providing a supraglottic airway having a shield capable of creating an airtight seal in the oropharyngeal region of a patient;
providing an esophageal blocker;
placing said supraglottic airway in a patient in the oropharyngeal region of said patient to provide the patient with an artificial airway;
after said placing, moving said esophageal blocker relative to said supraglottic airway in such a manner that a portion of said esophageal blocker is guided by a guide structure external the respiratory tube of said supraglottic airway past said supraglottic airway and into the esophagus of said patient; and
after said moving, deploying said esophageal blocker in said esophagus to block said patient's esophagus.

* * * * *